United States Patent [19]

May

[11] Patent Number: 5,116,376
[45] Date of Patent: May 26, 1992

[54] KNEE PROSTHESIS
[75] Inventor: Denis R. W. May, Stanmore, United Kingdom
[73] Assignee: University College London, London, England
[21] Appl. No.: 422,544
[22] Filed: Oct. 17, 1989
[30] Foreign Application Priority Data
Oct. 18, 1988 [GB] United Kingdom ............... 8824383
[51] Int. Cl.$^5$ ............................................. A61F 2/38
[52] U.S. Cl. ................................................... 623/20
[58] Field of Search ....................... 623/20, 16, 18, 20, 623/21, 23

[56] References Cited
U.S. PATENT DOCUMENTS
4,216,549  8/1980  Hillberry et al. ..................... 623/20
4,224,697  9/1980  Murray et al. ........................ 623/20

FOREIGN PATENT DOCUMENTS
194326  3/1985  European Pat. Off. .
294298  5/1988  European Pat. Off. .

Primary Examiner—David Isabella
Attorney, Agent, or Firm—Oblon, Spivak, McClelland, Maier & Neustadt

[57] ABSTRACT

A knee prosthesis is provided which forces the femur and tibia apart on twisting of the knee so that weight applied through the knee has an untwisting action. A tibial member and an intermediate member are journalled together by peg which fits into socket. Opposite handed helical surfaces cam the members apart when the knee is twisted. A knee hinge is defined by the intermediate member and a female member.

8 Claims, 3 Drawing Sheets

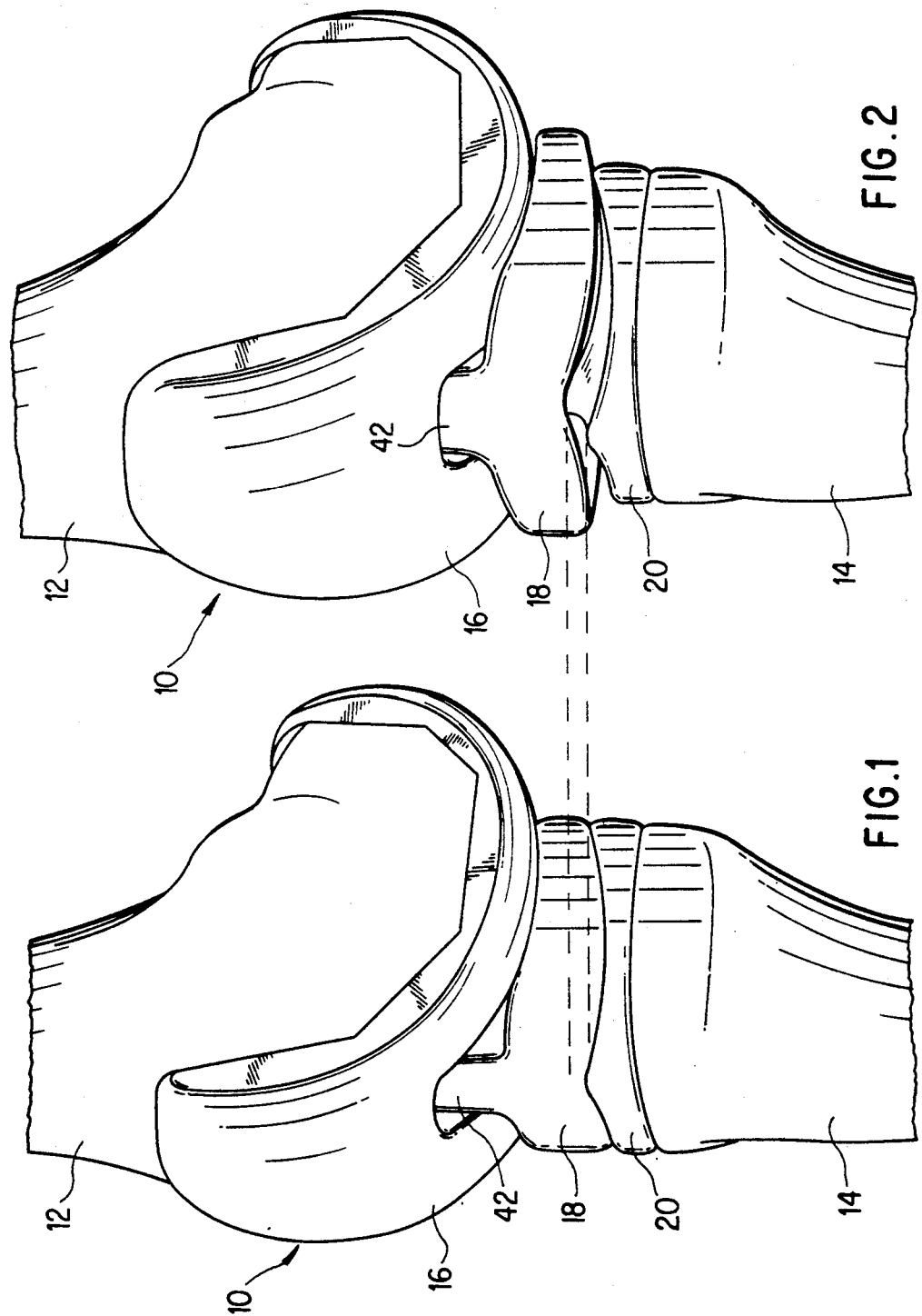

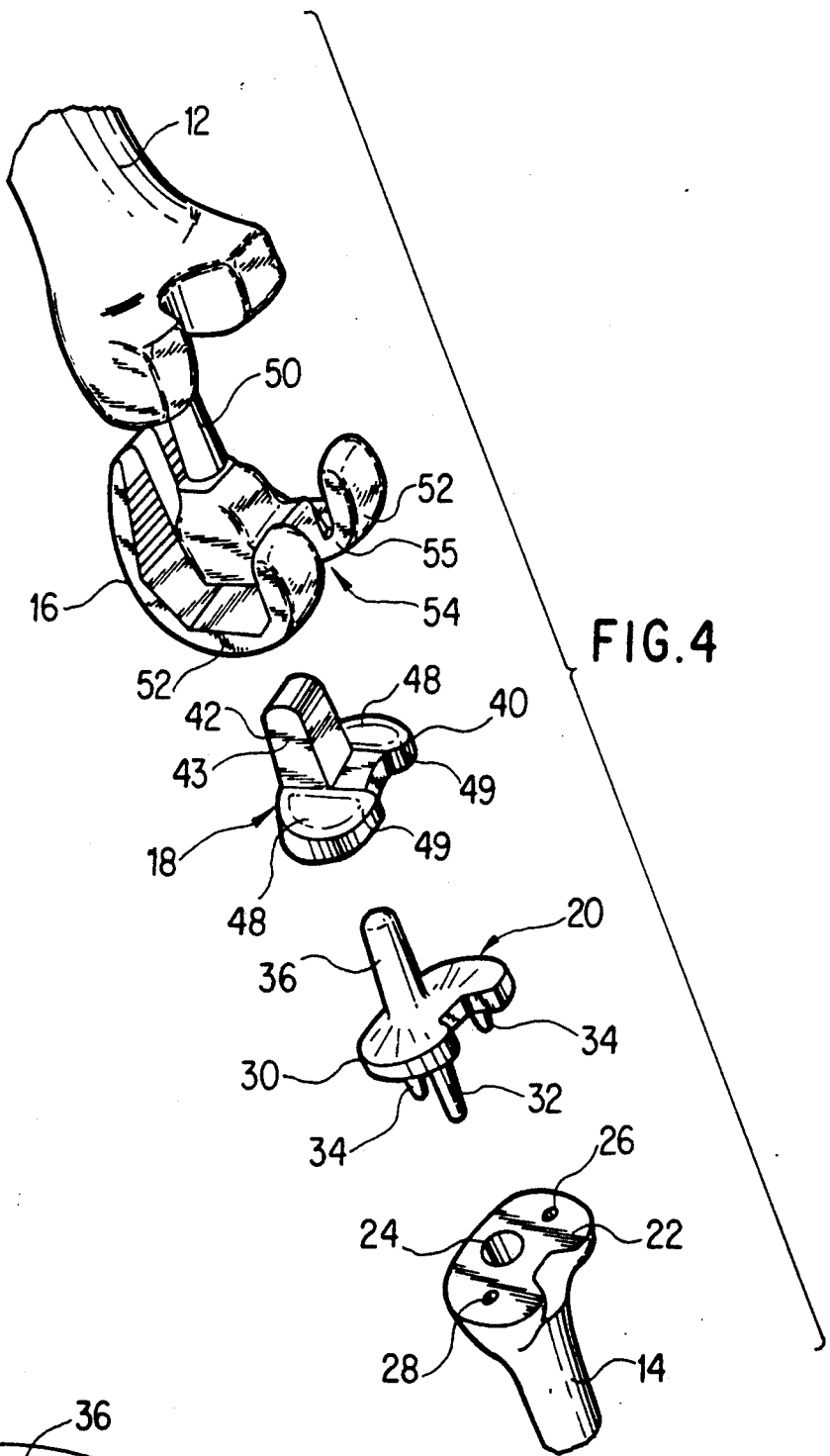
FIG.4
FIG.5
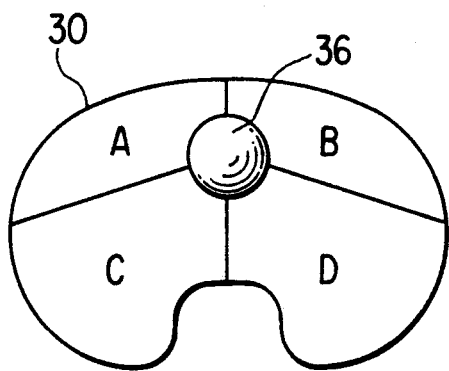

KNEE PROSTHESIS

BACKGROUND OF THE INVENTION

1. Field of the Invention

This invention relates to a knee prosthesis for fitting as an implant to a patient requiring knee replacement, for example because of arthritis or other degenerative desease.

SUMMARY OF THE INVENTION

One object of the invention is to provide a knee prosthesis that is less affected by torsional loads when implanted in the patient and hence has a lesser tendecy to work loose from the femoral and tibial bones.

A further object of the invention is to provide a prosthesis that can be used for revision cases where a previous knee has failed.

Further objects of the invention are to provide such a prosthesis that can be fitted with a minimal loss of bone stock, is of improved stability and defines a neutral position for the tibial and femoral bones while allowing limited twisting.

In one aspect the invention provides a knee prosthesis which forces the femur and tibia apart upon twisting of the knee so that weight applied through the knee has an returning action.

The invention further provides a human knee comprising femur and tibia members, first means defining a knee hinge and second means permitting twisting of the femur and tibia member about an axis generally orthogonal to the knee hinge and causing a movement of the femur and tibia members axially apart upon twisting them from a neutral position.

The knee prosthesis is generally of three principal components, with the superior member being a femoral member, the inferior member being a tibial member, and an intermediate member fitting between the femoral and tibial members. In such a structure, preferably, knee articulation occurs between the femoral member and the intermediate member and twisting about a direction generally orthogonal to the knee axis occurs between the intermediate member and the tibial member. The twisting is brought about, according to a feature of the invention, by opposed helical guide or cam surfaces on the intermediate and tibial members. By the use of helical surfaces the intermediate and tibial members are maintained in area contact rather than point contact to minimize in-service wear. In another feature, journal bearing means connects the intermediate and tibial members. Advantageously the journal bearing means is defined by an anteriorly located spindle on the tibial member which fits into a socket e.g. in an upstanding finger on the intermediate member, the femoral member having a cavity into which the finger can fit at some angular positions of the knee.

Preferably, lateral surfaces of the finger cooperate with adjoining surfaces of the femoral member to resist translational displacement or other relative movement of the tibia and femoral in a medial-lateral direction which might give rise to vulgus or varus deformity. Further, it is preferred that an anterior surface of the finger cooperates with portions of the cavity to define an extended position of the knee. In another feature, posterior surfaces of the cavity are shaped to remain on and roll over the finger as the knee flexes. The knee articulation may be defined by male condular surfaces on the femoral portion that make area contact with inferior female condular surfaces. Rear portions of the female condular surfaces may be raised to define a lip that limits relative translational displacement of the tibia and femur in a posterior direction. The knee prosthesis therefore has some stability, at least in its preferred forms, in an anterior/posterior plane.

BRIEF DESCRIPTION OF THE DRAWINGS

An embodiment of the invention will now be described, by way of example only, with reference to the accompanying drawings in which:

FIG. 1 is a view of a knee prosthesis and adjoining bones of an individual who has been fitted with the knee prosthesis in a normal state and with the leg unflexed;

FIG. 2 is a view as shown FIG. 1 but with the tibial part twisted at an angle to the femoral part;

FIG. 4 is an exploded view of the components of the knee; and

FIG. 5 is a plan view of a tibial member forming part of the knee.

DESCRIPTION OF THE PREFERRED EMBODIMENT

Figure 3:
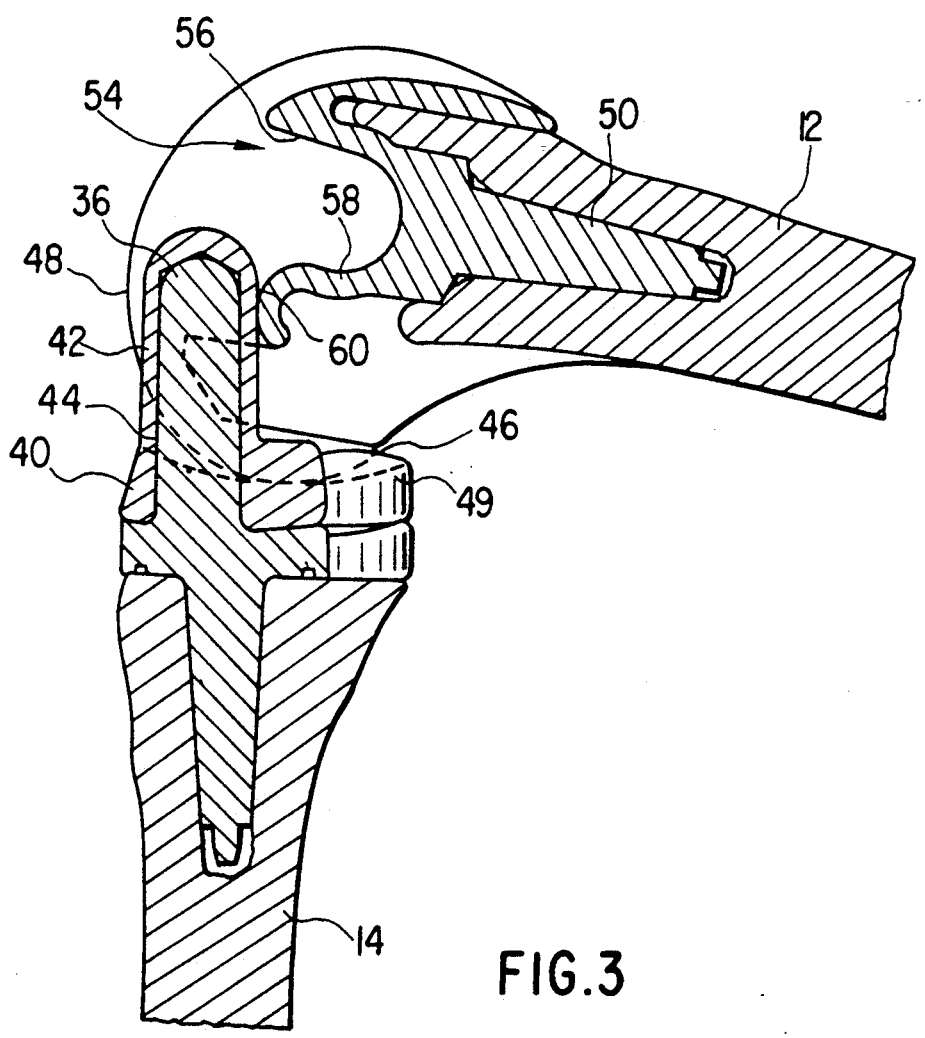
FIG. 3 is a view of the knee in a flexed position, the view being taken in section in an anterior/posterior plane.

In the drawings a knee prosthesis generally indicated by the reference numeral 10 fits between the femoral bone 12 and the tibial bone 14 of an individual who requires knee replacement, for example because the natural knee has deteriorated through arthritis. The knee prosthesis is made up of three interfitting components, a femoral member 16, an intermediate bearing member 18 and a tibial member 20. The tibial member 16 and the bearing member 18 form a first articulation which allows the femur and tibia bones 12 and 14 to undergo limited rotation about the longitudinal direction of the leg within the limits accommodated by the patient's muscles and ligaments which remain in place. The bearing member 18 and the tibial member 20 form a second articulation that permits knee flexion. A feature of this second articulation is the provision of medial-lateral support, support against relative movement in the anterior-posterior plane and the provision of area contact surfaces that minimize wear.

The tibial bone 12 is formed at its head by the surgeon with a plateau surface 22 (FIG. 4) that has three bores 24, 26 and 28. The tibial member 20 is of a cobalt/chrome/molybedum alloy (Stellite) or similar material that has good wear properties in an artificial knee and is resistant to body fluids. It has a tray portion 30 that covers the tibial plateau 22. The tray portion 30 is somewhat kidney shaped when viewed in plan to permit the posterior cruciate ligament to be preserved. From the lower face of the tray portion 30 there depends a central fixing spur or stem 32 and a pair of anti-rotation lugs 34 that fit into the bore 24 and into the bores 26, 28 respectively. The spur 32 and lugs 34 may be press fitted into the bores in the tibial bone 12 or they may be cemented in place with a bone cement as is known in the art. The lower face of the tray portion 30 is flanged to define a space that may be filled with beads bonded to the tray portion 30 and bonded together to provide interstices for ingrowth of bone. The upper surface of the tray portion 30 has an upstanding peg 36. As best seen in FIG. 5, the top surface of the tray portion 30 is formed with ramped surfaces A, D and B, C. The surfaces A and D are sectors of a first helical surface having a pitch of about 28 mm. The surfaces B and C are female sectors of an opposite hand helical surface having the same pitch. The two helices are concentric with the peg 36 that acts as a spindle of a bearing and the surfaces A, D and B, C coverage inwardly and downwardly at a small angle when viewed in section for stability of the overlying members. The adjacent surfaces A-C, C-D, D-B and B-A are smoothly flared into one another.

The bearing member 18 is of a wear-resistant low-friction physiologically acceptable plastics material such as ultra-high molecular weight polyethylene (Rhur-Chemie 1000) and has a plate-like body 40 conforming in plan to the outline of the tray portion 30 and an upstanding finger 42. A blind bore or socket 44 (FIG. 3) extends from the lower face of the body 40 into the finger 42 to receive the peg 36. A lower or follower face 46 of the body 40 has a male shape corresponding to the upper face of the tray portion 30. Thus when the tibial member 20 and the bearing member 18 are aligned, corresponding to a neutral position of the femoral and tibial bones 12, 14, the upper surface of the tray portion 30 and the lower face 46 of the bearing member 18 are in substantially continuous contact. Rotation of the tibial member 20 and bearing member 18 relative to one another in either angular direction causes the helical surfaces A, D or B, C to cam the members 18, 20 and hence also the members 16, 20 axially apart with the peg 36 sliding along the bore 44. When the patient's weight is on the leg, there is a restoring force tending to return the members 18, 20 to their neutral or untwisted position.

To either side of the finger 42, the upper face of the body 40 is formed with dished condular bearing surfaces 48. The femoral member 16 fits onto the end of the femoral bone 12, to which it conforms, by means of a fixing spur 50 which is received in a bore drilled into the femoral bone 12. It has condular bearing surfaces 52 on either side thereof and between which is defined a cavity 54 shaped to receive the finger 42 when the knee is unflexed, and to allow the finger 42 to move out of the cavity 54 as the knee moves to its fully flexed state. The finger 42 is a close fit in the medial-lateral plane into the cavity 54 and has planar lateral surfaces 43 which remain trapped either within the cavity 54 or within planar surfaces 55 leading to the cavity 54 that the finger 42 resists relative translational movement of the bearing member 18 and femoral member 16 in the medial-lateral plane and resists relative rotational movement. The anterior face 56 (FIG. 3) of the cavity 54 abuts a generally planar or gently curved front face of the finger 42 as the leg unflexes to limit extension of the leg, generally at about 5 hyperextension. The posterior face 58 of the cavity 54 leads to a lower flared or radiused surface 60 that is concentric with portions of the condular bearing surfaces 48 so that at high angles of flexion the radiused surface 60 seats on and rolls over or wipes the rear face of the finger 42 which is also planar so that the finger 42 supports the femoral member 16 at high angles of flexion. Thereby the femoral and tibial bones 12, 14 are stabilized against relative translational movement in an anterior direction at high angles of flexion. The condular bearing surfaces 48 of the tray portion 40 are relatively extensive and deeply dished with, in particular, a rising posterior portion defining a rear lip 49. Cooperation between the lip 49 and the condular bearing surfaces 52 prevents or limits relative translational movement of the femoral and tibial bones 12, 14 in the posterior direction, there typically being 3-4 mm of laxity to prevent the knee locking.

It will be appreciated that the knee prosthesis described above may be required in a range of sizes to accommodate different patients.

I claim:

1. A knee prosthesis which comprises: femoral and tibial members interconnected by first means defining a knee hinge having an axis, and second means comprising an intermediate member and configured for permitting twisting of knee, said second means comprising:
   (a) bearing means defining an articulation surface of said knee about an axis generally at right angles to a knee hinge axis and;
   (b) means defining a pair of oppositely handed concave helical surfaces, and a pair of condylar members having convexly curved surfaces that are complementary to and ride over said helical surfaces so that when said knee is twisted from a neutral position each of said condylar members rides over the respective helical surfaces forcing the femur and tibia of a user of the prosthesis apart, such that weight applied through the knee has an untwisting action which returns the femoral and tibial members to a neutral position.

2. A prosthesis according to claim 1, wherein said tibial member comprises stabilizing means for stabilizing the femoral and tibial members against relative movement in a medial-lateral plane.

3. A prosthesis according to claim 1, wherein said tibial member includes stabilizing means for stabilizing the femoral and tibial members against relative movement in an anterior/posterior plane.

4. A prosthesis according to claim 1, wherein the intermediate and tibial members are interconnected by journal bearing means.

5. A prosthesis according to claim 4, wherein the journal bearing means is defined by an anteriorly located spindle on the tibial member which fits into an upstanding finger on the intermediate member, the femoral member having a cavity into which the finger fits at unflexed angular positions of the knee.

6. A prosthesis according to claim 5, wherein lateral surfaces of the finger cooperate with adjoining surfaces of the femoral member to limit relative movement of the femoral and tibial members in a medial-lateral direction.

7. A prosthesis according to claim 6, wherein an anterior surface of the finger engages with portions of the cavity in an extended position of the knee.

8. A prosthesis according to claim 6, wherein a posterior region of the cavity leads to an exterior convexly curved region of the femoral member which is shaped to remain on and roll over the finger as the knee flexes.

* * * * *